(12) United States Patent
Avitsian et al.

(10) Patent No.: US 10,675,425 B2
(45) Date of Patent: Jun. 9, 2020

(54) REVERSIBLE AIRWAY DEVICE AND RELATED METHOD FOR VENTILATING A SUBJECT

(71) Applicants: THE CLEVELAND CLINIC FOUNDATION, Cleveland, OH (US); Parker Hannifin Corporation, Mayfield Hts., OH (US)

(72) Inventors: Rafi Avitsian, Solon, OH (US); Andrew Zura, Broadview Hts., OH (US); Ricardo Gonzalez, Valparaiso, IN (US); Michael Collinson, Camarillo, CA (US); Gino Banco, Lyndhurst, OH (US); Marijan Matakovic, Schererville, IN (US)

(73) Assignees: THE CLEVELAND CLINIC FOUNDATION, Cleveland, OH (US); PARKER HANNIFIN CORPORATION, Cleveland, OH (US)

( * ) Notice: Subject to any disclaimer, the term of this patent is extended or adjusted under 35 U.S.C. 154(b) by 876 days.

(21) Appl. No.: 14/795,932

(22) Filed: Jul. 10, 2015

(65) Prior Publication Data
US 2015/0314094 A1 Nov. 5, 2015

Related U.S. Application Data

(63) Continuation-in-part of application No. 14/048,343, filed on Oct. 8, 2013.
(Continued)

(51) Int. Cl.
*A61M 16/04* (2006.01)
*A61B 1/267* (2006.01)
*A61B 1/00* (2006.01)

(52) U.S. Cl.
CPC ..... *A61M 16/0488* (2013.01); *A61B 1/00135* (2013.01); *A61B 1/267* (2013.01);
(Continued)

(58) Field of Classification Search
CPC .............. A61M 16/00; A61M 16/0054; A61M 16/04–0463; A61M 16/0475–0497;
(Continued)

(56) References Cited

U.S. PATENT DOCUMENTS 4,509,514 A * 4/1985 Brain ................ A61M 16/0409
128/207.15
5,339,808 A 8/1994 Don Michael
(Continued)

FOREIGN PATENT DOCUMENTS

CN 1051511 A 8/1990
CN 1051511 A 5/1991
(Continued)

OTHER PUBLICATIONS

Office Action for corresponding on Application No. 201380063063.5, dated Jun. 8, 2017, 3 pages.
(Continued)

*Primary Examiner* — Michael J Tsai
*Assistant Examiner* — Ned T Heffner
(74) *Attorney, Agent, or Firm* — Tarolli, Sundheim, Covell & Tummino LLP

(57) ABSTRACT

A reversible airway device can include a tubular guide, a laryngeal mask, and an endotracheal tube. The tubular guide can have a distal end portion, a proximal end portion, and a first passageway extending between the distal and proximal end portions. The tubular guide can further include a first longitudinal seam. The laryngeal mask can be attached to the distal end portion of the tubular guide. The laryngeal mask can include an opening in fluid communication with the first
(Continued)

passageway. The laryngeal mask can further include a second longitudinal seam. The endotracheal tube can be slidably disposed within the first passageway and have a second passageway. The first and second longitudinal seams can be adapted to permit ingress and egress of the tubular guide from the airway without detaching the endotracheal tube from a ventilation source.

12 Claims, 13 Drawing Sheets

Related U.S. Application Data

(60) Provisional application No. 62/022,834, filed on Jul. 10, 2014.

(52) U.S. Cl.
CPC ........ *A61M 16/04* (2013.01); *A61M 16/0409* (2014.02); *A61M 16/0447* (2014.02); *A61M 16/0434* (2013.01); *A61M 16/0477* (2014.02)

(58) Field of Classification Search
CPC .......... A61M 16/10; A61M 16/14–147; A61M 25/10; A61M 25/1052; A61M 25/024; A62B 7/00–14; A62B 9/06
See application file for complete search history.

(56) References Cited

U.S. PATENT DOCUMENTS

| | | | |
|---|---|---|---|
| 5,477,851 A * | 12/1995 | Callaghan | A61M 16/04 128/200.23 |
| 5,937,859 A * | 8/1999 | Augustine | A61B 1/267 128/200.26 |
| 6,079,409 A | 6/2000 | Brain | |
| 6,634,354 B2 | 10/2003 | Kent | |
| 7,174,889 B2 | 2/2007 | Boedeker et al. | |
| 7,938,118 B2 | 5/2011 | Kessler | |
| 8,887,716 B2 | 11/2014 | Dubach | |
| 2001/0032646 A1 | 10/2001 | Christopher | |
| 2005/0051175 A1 | 3/2005 | Brain | |
| 2005/0081861 A1 | 4/2005 | Nasir | |
| 2005/0139220 A1 | 6/2005 | Christopher | |
| 2008/0257356 A1 | 10/2008 | Swick | |
| 2009/0090356 A1 | 4/2009 | Cook | |
| 2012/0090609 A1 | 4/2012 | Dubach | |
| 2015/0165148 A1 | 6/2015 | Kozlowski et al. | |

FOREIGN PATENT DOCUMENTS

| | | |
|---|---|---|
| EP | 0500778 B1 | 2/1997 |
| GB | 2472063 A | 1/2011 |
| JP | 501660 A | 4/1993 |
| JP | 10314308 A | 12/1998 |
| WO | 9107201 A1 | 5/1991 |
| WO | 2009/025843 A1 | 2/2009 |
| WO | 2012127435 A1 | 9/2012 |

OTHER PUBLICATIONS

Search Report corresponding to Int'l Patent Application No. CN 201380063063.5, dated Apr. 27, 2017.
Japanese Office Action for corresponding Japanese Application No. 2015-536831, dated Dec. 5, 2017, pp. 1-4.
International Search Report and Written Opinion for PCT/US2015/039858, dated Jan. 7, 2016, pp. 1-19.
PCT Invitation to Pay Additional Fees for PCT/US2015/039858, dated Oct. 13, 2015, pp. 1-6.
PCT Communication Relating to the Results of the Partial International Search, dated Jan. 29, 2014, pp. 5-6.
Patent Office of the People's Republic of China Search Report for Application No. 2013800630635, pp. 1-2.
Office Action for corresponding Japanese Patent App. No. 2015-536831, dated Jan. 31, 2017, pp. 1-2.
Office Action for corresponding Chinese Patent App. No. 201380063063.5, dated Dec. 5, 2016, pp. 1-7.

* cited by examiner

REVERSIBLE AIRWAY DEVICE AND RELATED METHOD FOR VENTILATING A SUBJECT

RELATED APPLICATIONS

This application is a continuation-in-part of U.S. patent application Ser. No. 14/048,343, filed Oct. 8, 2013, the entirety of which is hereby incorporated by reference for all purposes. This application also claims the benefit of U.S. Provisional Patent Application Ser. No. 62/022,834, filed Jul. 10, 2014, the entirety of which is hereby incorporated by reference for all purposes.

TECHNICAL FIELD

The present disclosure relates generally to the field of anesthesiology and, more particularly, to a reversible airway device and related method for ventilating a subject using the airway device that does not risk disconnection or loss of the patient's airway during ventilation.

BACKGROUND

Airway devices are widely used in hospital surgical environments to provide respiratory assistance and ventilate patents during medical procedures. While there are a multitude of airway devices currently on the market, one popular airway device is a sub-glottic device, also known as an endotracheal tube and another is a supra-glottic support device, such as a laryngeal mask. While the use of these devices is widespread, there are disadvantages associated with each of these devices.

Endotracheal tubes, for example, are used to ventilate patients requiring anesthesia and/or respiratory assistance. An example of a conventional endotracheal tube is a plastic tube, which is inserted into a subject's mouth, passed down the trachea through the vocal cords, and lodged in the trachea proximal to (or above) the lungs. The endotracheal tube may have a cuff or balloon portion surrounding the circumference of the endotracheal tube near the distal end that rests in the subject's trachea. After the endotracheal tube has been inserted properly, the cuff may be inflated to seal against the wall of the trachea. Once sealed, positive pressure ventilation may be used to provide respiratory assistance and, if desired, anesthesia or other gas, gas mix, etc., to the patient though the endotracheal tube via a ventilator. The cuff provides a seal that tends to block liquids and solids from passing along the outside of the endotracheal tube between the tube and the trachea wall and entering the subject's lungs.

A supra-glottic support device typically includes a hollow tube (sometimes referred to as a tubular guide, tube or guide) and a laryngeal mask. The laryngeal mask of the laryngeal mask is intended to fit in the mouth of a patient to cover the openings and block the fluid path to and from the esophagus and stomach, and provide a fluid path to the trachea and lungs for ventilating the patient. The laryngeal mask may be positioned without requiring a physician to view the airway directly. The laryngeal mask has an inflatable cuff or rim area. Once the laryngeal mask is placed into the subject's mouth, the cuff can be inflated to seal against the walls of the inside of the mouth and pharynx, if positioned properly, to block flow to and from the esophagus. A flexible, membranous support material extends from the cuff to form a recessed area, e.g., a space or volume, into which a gas mix can be pumped through the tube or other instrumentality of the laryngeal mask to provide the requisite air and/or anesthesia to the patient. The tube is of relatively large diameter, as compared to the usually relatively narrower diameter passage of a conventional endotracheal tube, and such relatively large diameter facilitates gas mix and exhalant flow with relatively minimal interference, pressure drop, etc. The support material supports the cuff from the tube. Thus, the laryngeal mask can be used to supply a gas mix to the recessed area and from there to the trachea.

In patients that require ventilation with an airway device (e.g., critically ill or injured subjects), it is important to maintain a continuous airway. In such patients, if ventilation begins with a supra-glottic support device (e.g., a laryngeal mask) and intubation subsequently becomes necessary, the supra-glottic support device must be removed from the patient so that an endotracheal tube can be placed or an interchangeable smaller diameter tube placed before changing to the endotracheal tube. Doing so, however, requires that the patient's airway be temporarily disrupted while also increasing the risk that the patient's airway may not be recovered. Additionally, placing an endotracheal tube requires the skill of an experienced medical professional, who may not be present in all circumstances in which unexpected intubation is required.

SUMMARY

The present disclosure relates generally to the field of anesthesiology and, more particularly, to a reversible airway device and related method for ventilating a subject using the airway device that does not risk disconnection or loss of the patient's airway during ventilation.

One aspect of the present disclosure relates to a reversible airway device that can comprise a tubular guide, a laryngeal mask, and an endotracheal tube. The tubular guide can have a distal end portion, a proximal end portion, and a first passageway extending between the distal and proximal end portions. The tubular guide can further include a first longitudinal seam. The laryngeal mask can be attached to the distal end portion of the tubular guide. The laryngeal mask can include an opening in fluid communication with the first passageway. The laryngeal mask can further include a second longitudinal seam. The endotracheal tube can be slidably disposed within the first passageway and have a second passageway. The first and second longitudinal seams can be adapted to permit ingress and egress of the tubular guide from the airway without detaching the endotracheal tube from a ventilation source.

Another aspect of the present disclosure relates to a reversible airway device comprising a tubular guide, a laryngeal mask, an endotracheal tube, and an inflatable guide member. The tubular guide can have a distal end portion, a proximal end portion, and a first passageway extending between the distal and proximal end portions. The laryngeal mask can be attached to the distal end portion of the tubular guide. The laryngeal mask can include an opening in fluid communication with the first passageway. The endotracheal tube can be slidably disposed within the first passageway. The endotracheal tube can have a second passageway. The inflatable guide member can be configured for selectively directing the endotracheal tube at a desired angle when the endotracheal tube is urged through the opening.

Another aspect of the present disclosure can include a reversible airway device comprising a tubular guide, a laryngeal mask, an endotracheal tube, and a ring-shaped clip. The tubular guide can have a distal end portion, a proximal end portion, and a first passageway extending between the distal and proximal end portions. The laryngeal mask can be attached to the distal end portion of the tubular guide. The laryngeal mask can include an opening in fluid communication with the first passageway. The endotracheal tube can be slidably disposed within the first passageway and include a second passageway. The ring-shaped clip can be associated with the proximal end portion of the tubular guide. The clip can be configured to maintain the endotracheal tube in the center of the first passageway.

Another aspect of the present disclosure can relate to a method for easing transition of a sedated patient to wakefulness, the sedated patient being intubated with an endotracheal tube having a distal cuff connected thereto. One step of the method can include placing a tubular guide over the endotracheal tube. The tubular guide can have a distal end portion, a proximal end portion, and a first passageway extending between the distal and proximal end portions. The tubular guide can further include a laryngeal mask attached to the distal end portion of the tubular guide. The laryngeal mask can include an opening in fluid communication with the first passageway. The tubular guide can be advanced over the endotracheal tube until the laryngeal mask is located in the pharynx above the glottis. Next, the laryngeal mask can then be inflated. The endotracheal tube can then be withdrawn so that the distal cuff is disposed within the distal end portion of the tubular guide. Optionally, the distal cuff of the endotracheal tube can then be inflated.

Another aspect of the present disclosure relates to a method for intubating a subject. One step of the method can include providing a reversible airway device. The airway device can include a tubular guide, a laryngeal mask, an endotracheal tube and a sealing mechanism. The tubular guide can have a distal end portion, a proximal end portion, and a first passageway extending between the distal and proximal end portions. The laryngeal mask can be attached to the distal end portion and include an opening in fluid communication with the first passageway. The tubular guide and the laryngeal mask can include first and second longitudinal seams. The endotracheal tube can be slidably disposed within the first passageway and have a second passageway. The sealing mechanism can be disposed in the first passageway. Next, the laryngeal mask can be inserted into the subject so that an airtight seal is formed between the laryngeal mask and the airway of the subject. The endotracheal tube can then be deployed so that a distal end of the endotracheal tube is positioned below the vocal cords of the subject, whereafter, a distal cuff of the endotracheal tube can be inflated. A flow of gas through the second passageway is uninterrupted during the inserting and deploying steps.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
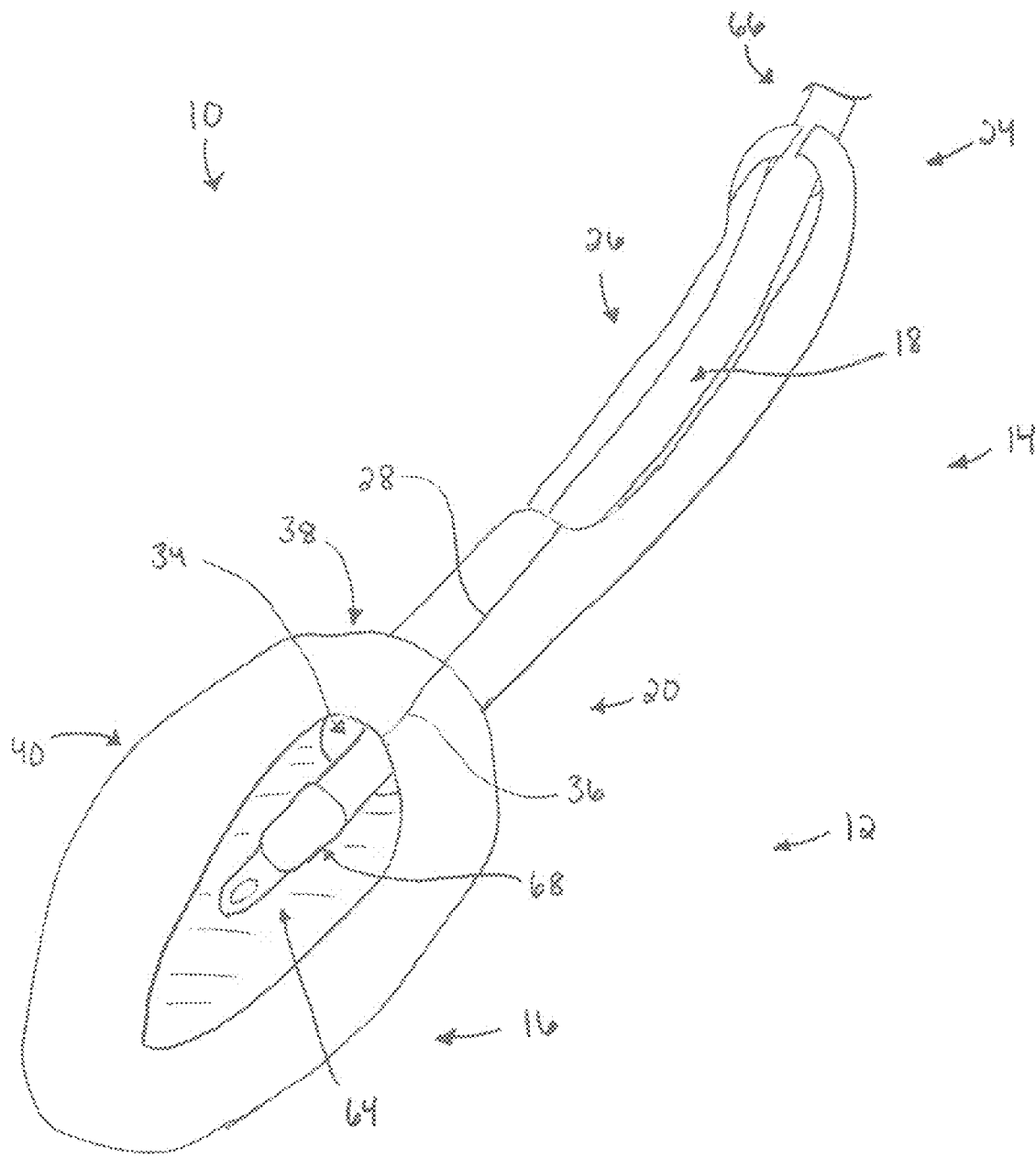
FIG. 1 is a perspective view of a reversible airway device constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "ventilating" or "ventilate" can refer to providing breathable air or oxygen, for example, and removing gas, etc., e.g., exhalant exhaled by a subject, and providing anesthesia and/or other materials to and/or from the lungs of a subject. The terms can also have the usual meaning as used in the field of medicine. The various gases, e.g., oxygen, air, anesthesia, etc., alone or in combination sometimes are referred to below collectively as a gas mixture.

As used herein, the terms "subject" and "patient" can be used interchangeably and refer to any warm-blooded organism including, but not limited to, human beings, pigs, rats, mice, dogs, goats, sheep, horses, monkeys, apes, rabbits, cattle, etc.

Overview

The present disclosure relates generally to the field of anesthesiology and, more particularly, to a reversible airway device and related method for ventilating a subject using the airway device that does not risk disconnection or loss of the patient's airway during ventilation. As representative of one aspect of the present disclosure, FIG. 1 illustrates a reversible airway device 10 for establishing an artificial airway and providing continuous ventilation in a subject when needed. Existing airway devices and associated methods for ventilating subjects involve the introduction of an endotracheal tube through a supra-glottic airway support device. This is time consuming, involves multiple devices, entails ventilation stoppage, and requires a high level of medical expertise. Advantageously, the present disclosure integrates both sub-glottic and supra-glottic support components that can easily provide intubation (with or without fibroscopic direct visualization guidance) and, when needed, be quickly changed to function as a supra-glottic airway support while not compromising ventilation.

Reversible Airway Devices

One aspect of the present disclosure can include a reversible airway device 10. As discussed below, certain components of the airway device 10 can be constructed in an identical or similar manner as the reversible airway device disclosed in U.S. patent application Ser. No. 14/048,343 (hereinafter, "the '343 application"), filed Oct. 8, 2013. The reversible airway device 10 of the present disclosure can generally include a supra-glottic airway support 12 (e.g., comprising a tubular guide 14 and a laryngeal mask 16), an endotracheal tube 18, and a sealing mechanism. By "reversible", it is meant that an artificial airway provided by the supra-glottic airway support 12 can be readily exchanged for an artificial airway provided by the endotracheal tube 18 without removing or disconnecting any component(s) of the airway device 10, and while maintaining continuous, uninterrupted ventilation. In other words, the term "reversible" can refer to the ability of the airway device 10 to be changed from a supra-glottic airway support 12 to an endotracheal tube 18, and then back to a supra-glottic airway support, without compromising ventilation. As discussed in more detail below, the airway device 10 of the present disclosure can be used for all indications of a supra-glottic airway support device where there is a possibility that endotracheal intubation may be necessitated (e.g., in trauma or critically ill patients).

As shown in FIG. 1, one component of the airway device 10 includes a supra-glottic airway support 12. The supra-glottic airway support 12 can include a tubular guide 14 (e.g., a hollow tube) and a laryngeal mask 16 that surrounds, and is connected to, a distal end portion 20 of the tubular guide. The tubular guide 14 includes a first passageway 22 (FIG. 2B) that extends between the distal end portion 20 (FIG. 1) and a proximal end portion 24 thereof. The first passageway 22 of the tubular guide 14 is sized and dimensioned to receive the endotracheal tube 18. The proximal end portion 24 of the tubular guide 14 may be conveniently of any size and shape to secure a variety of attachments (not shown) to the tubular guide (e.g., a syringe, an endoscope probe, a gas mix supply connection to receive a gas mix for ventilating, anesthetizing, etc., a patient, a drainage tube, etc.). When in use, the proximal end portion 24 of the tubular guide 14 remains outside of the subject's mouth and, therefore, is accessible to a healthcare provider (e.g., physician, nurse or other individual).

Also partially extending between the distal and proximal end portions 20 and 24 of the tubular guide 14 is a longitudinal slot 26. The longitudinal slot 26 can serve as a rapid and convenient means for introducing the endotracheal tube 18 into the tubular guide 14. It will be appreciated that the longitudinal slot 26 can be located on either the anterior or posterior portion of the tubular guide 14.

Figure 2A:
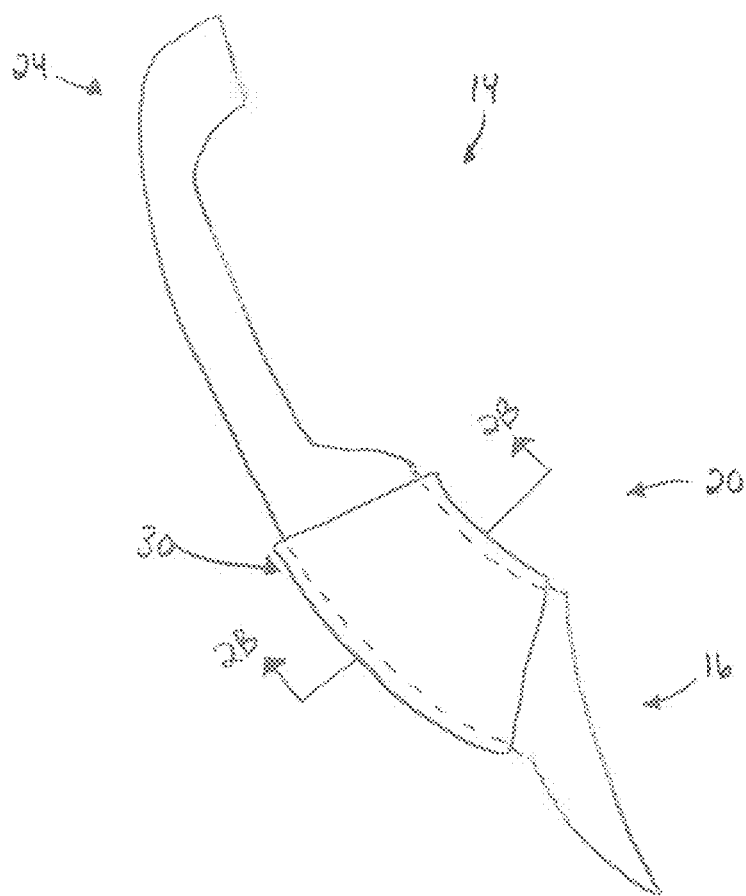
FIG. 2A is a schematic illustration showing a cuff placed about a distal end portion of a tubular guide comprising the reversible airway device in FIG. 1.
Figure 2B:
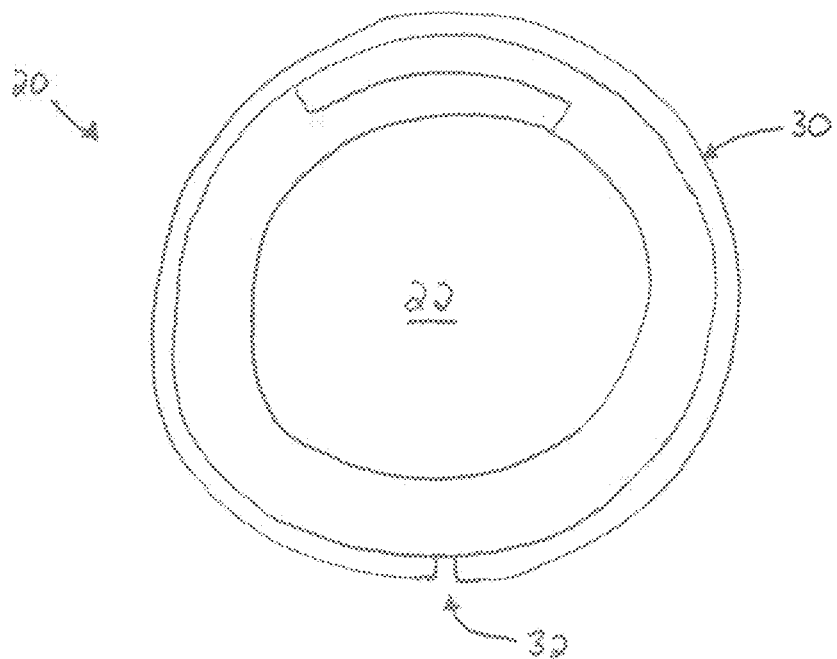
FIG. 2B is a cross-sectional view taken along Line 2B-2B in FIG. 2A.

As shown in FIG. 1, the tubular guide 14 can include a first longitudinal seam 28. The first longitudinal seam 28 can extend across all or only a portion of the distal end portion 20 of the tubular guide 14. The first longitudinal seam 28 can be a line, groove, or ridge formed by the abutment of opposing edges of the tubular guide 14. To form the first longitudinal seam 28, opposing edges of the tubular guide 14 can be joined using one or a combination of techniques, such as heat or adhesive bonding (e.g., crimping) and stitching. Additionally or alternatively, the first longitudinal seam 28 can be formed by virtue of the tubular guide wall configuration. As shown in FIG. 2B, for example, the first longitudinal seam 28 can be formed from overlapping portions of the tubular guide wall. This configuration also provides the tubular guide 14 with a relatively smooth inner surface. The opposing edges can be joined such that selective application of a desired force (e.g., tactile force) causes the first longitudinal seam 28 to split apart and thereby expose the first passageway 22 of the tubular guide 14. As explained in more detail below, the first longitudinal seam 28 advantageously allows ingress and egress of the tubular guide 14 from the airway of a patient without detaching the endotracheal tube 18 from a ventilation source.

In another aspect, the airway device 10 can additionally or optionally include a removable sleeve 30 (FIGS. 2A-B) configured to prevent unintended separation of the first longitudinal seam 28. The removable sleeve 30 can have a substantially tubular shape and be sized and dimensioned to fit over all or only a portion of the distal end portion 20 of the tubular guide 14. The removable sleeve 30 can have a rigid or semi-rigid configuration that allows it to slide off of the tubular guide 14 when separation of the first longitudinal seam 28 is desired. In some instances, the removable sleeve 30 can include a longitudinal slit 32 that can be separated to facilitate removal of the sleeve from the tubular guide 14. In other instances, the longitudinal slit 32 may be absent from the removable sleeve 30. In such instances, the sleeve 30 can be removed from the tubular guide 14 by sliding the sleeve in a proximal direction over the proximal end portion 24 of the airway device 10.

Typically, the size and shape of the tubular guide 14 are selected so that the distal end portion 20 can be readily inserted into a subject's mouth and upper airway with the laryngeal mask 16 substantially sealing the laryngeal inlet of the subject. The tubular guide 14 is generally J-shaped to follow the profile of a typical subject's airway through the mouth, over the tongue, and into the laryngopharynx region of the subject just above the opening to the larynx. The tubular guide 14 is shaped to prevent the subject's tongue and pharynx from obstructing access to the trachea. The tubular guide 14 can be made from one or a combination of materials, such as various thermoplastic or thermoset polymers, with sufficient strength and rigidity to keep the subject's teeth apart and to prevent the subject from biting down and collapsing the tubular guide, but with sufficient flexibility to allow comfortable and easy placement in the subject. The tubular guide 14 (as well as the laryngeal mask 16) can also be sized to accommodate a wide range of patient sizes (e.g., pediatric patients).

Figure 3A:
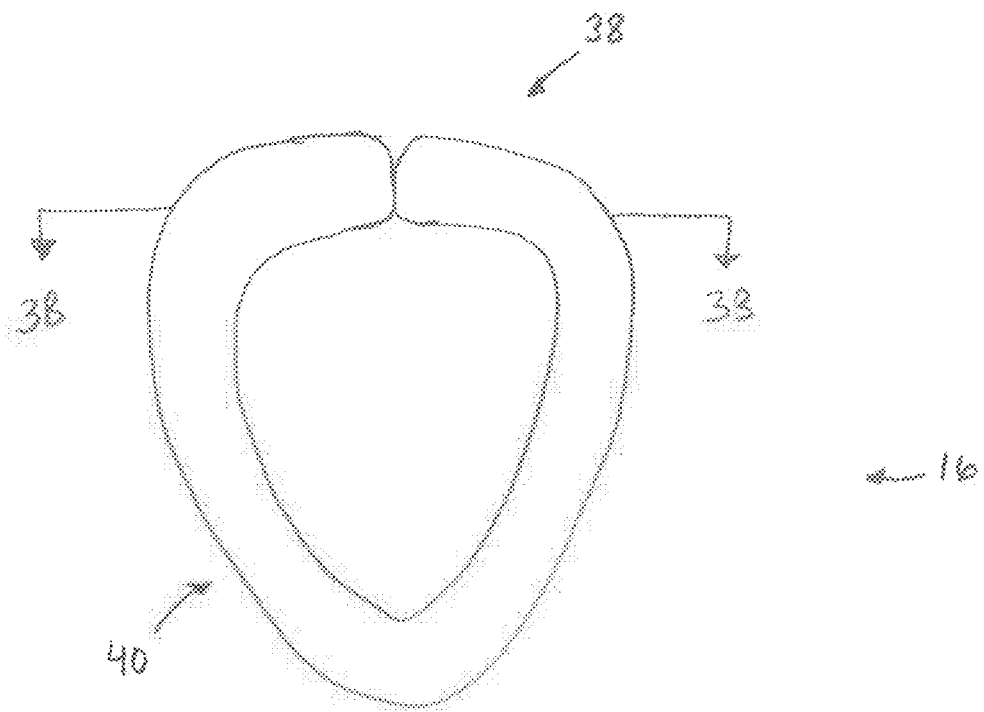
FIG. 3A is a schematic illustration showing an alternative configuration of the laryngeal mask in FIG. 1.
Figure 3B:
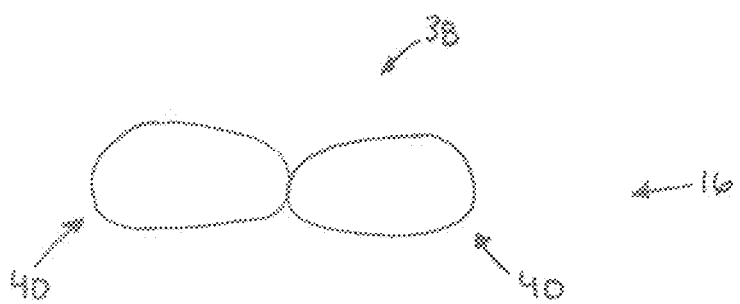
FIG. 3B is a cross-sectional view taken along Line 3B-3B in FIG. 3A.
Figure 4A:
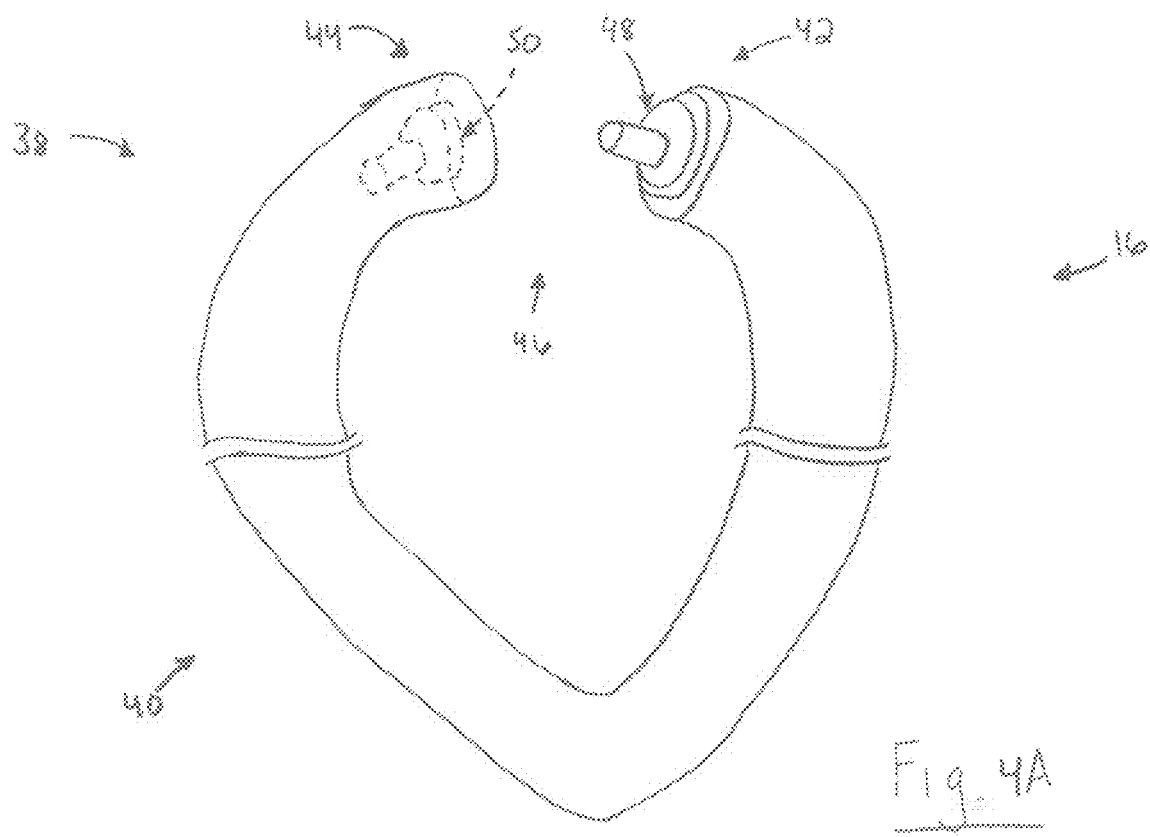
FIGS. 4A-B are schematic illustrations showing another alternative configuration of a laryngeal mask comprising the reversible airway device in FIG. 1.
Figure 4B:
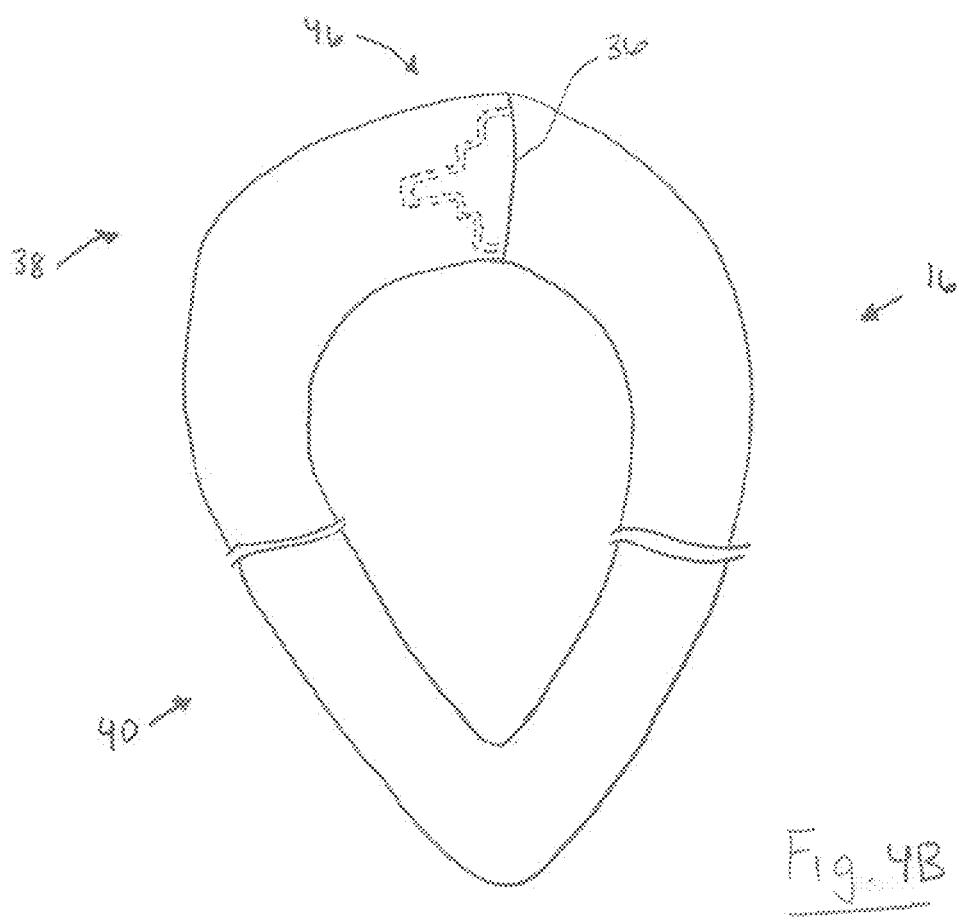

In another aspect, the laryngeal mask 16 can include an opening 34 in fluid communication with the first passageway 22. In some instances, the opening 34 can be beveled to substantially match the angle of the subject's laryngeal inlet after insertion of the supra-glottic airway support 12 into the subject's airway. The supra-glottic airway support 12 can also include a second longitudinal seam 36. The second longitudinal seam 36 can extend across all or only a portion of an upper portion 38 of the laryngeal mask 34. The second longitudinal seam 36 can be a line, groove, or ridge formed by the abutment of opposing edges at least partially defining the upper portion 38 of the laryngeal mask 16. To form the second longitudinal seam 36, opposing portions of the laryngeal mask 16 can be joined using one or a combination of techniques, such as heat or adhesive bonding (e.g., crimping) (FIGS. 3A-B) and stitching. For example, an inflatable portion 40 (FIGS. 4A-B) of the laryngeal mask 16 can comprise first and second free end portions 42 and 44 that, when joined, form the second longitudinal seam 36. As shown in FIGS. 4A-B, the first and second free end portions 42 and 44 can define a connecting mechanism 46 comprising a connecting member 48 associated with the first free end portion, and a port member 50 associated with the second free end portion, which is configured to receive the connecting member. The opposing portions 42 and 44 of the inflatable portion 40 can be joined such that selective application of a desired force (e.g., tactile force) causes the second longitudinal seam 36 to split apart and thereby expose the opening 34 of the laryngeal mask 16. Like the first longitudinal seam 28, the second longitudinal seam 36 advantageously allows ingress and egress of the tubular guide 14 from the airway of a patient without detaching the endotracheal tube 18 from a ventilation source. It will be appreciated that, in some instances, the first and second longitudinal seams 28 and 36 can form a single, continuous seam.

Figure 6:
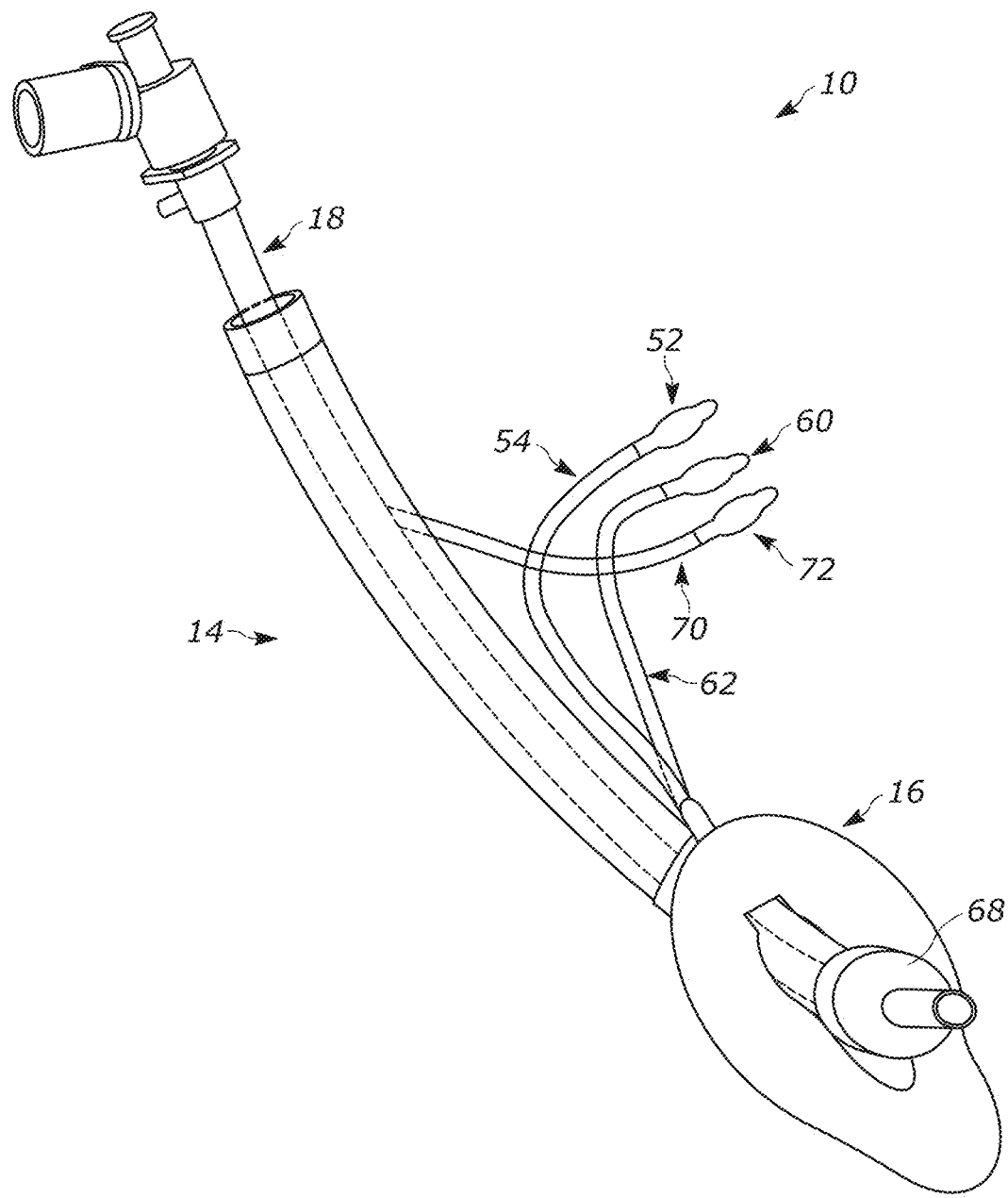
FIG. 6 is a perspective view of the reversible airway device in FIG. 5.

The supra-glottic airway support 12 can further include an inflation tube 52 (FIG. 6) and an air valve 54 for inflating and deflating the inflatable portion 40 or member (e.g., a cuff) of the laryngeal mask 16. Additionally or optionally, the laryngeal mask 16 can include one or more suction ports (not shown). Each suction port can be in fluid communication with a vacuum or source of negative pressure (not shown). In one example, the laryngeal mask 16 can include one or more suction ports circumferentially spaced about the perimeter of the inflatable portion 40. The suction port(s) can be used to remove secretions or fluid from the patient's airway during use of the airway device 10.

Figure 5:
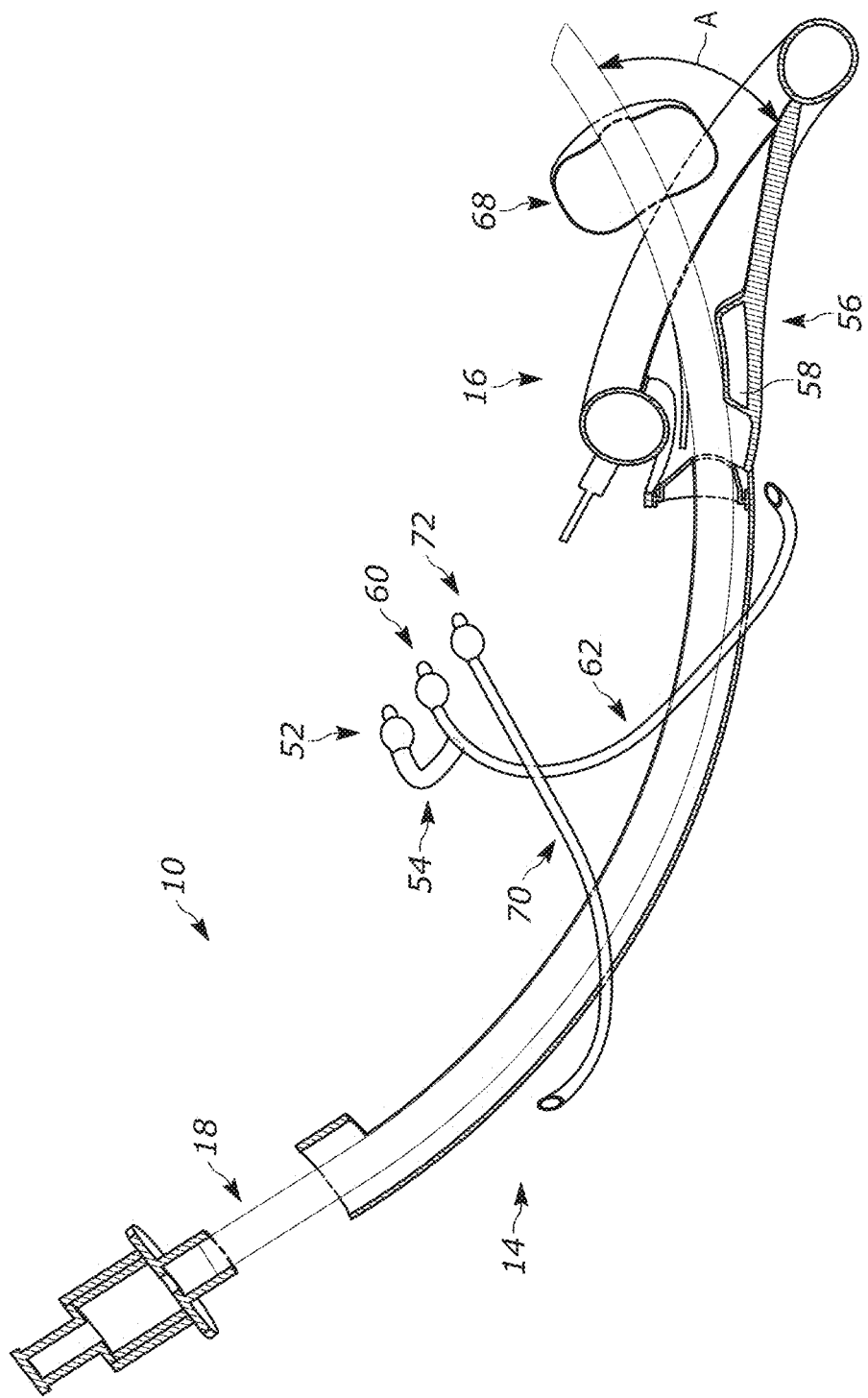
FIG. 5 is a cross-sectional view showing an alternative configuration of the reversible airway device in FIG. 1.

In another aspect, the laryngeal mask 16 (FIG. 5) can include an inflatable guide member 56 for directing the endotracheal tube 18 at a desired angle (e.g., to substantially match the angle of the subject's laryngeal inlet). The inflatable guide member 56 can comprise a piece of thermoplastic or thermoset polymer, for example, that defines an air-tight chamber 58 disposed on a surface of the laryngeal mask 16 (e.g., adjacent the opening 34). In one example, the inflatable guide member 56 can have a rectangular shape and include a U-shaped cross-sectional profile. The air-tight chamber 58 can be in fluid communication with an air valve 60 (FIG. 6) via an inflation tube 62 that enables selective inflation and deflation of the inflatable guide member 56. Similar to the guide member disclosed in the '343 application, the angle A (FIG. 5) formed by the inflatable guide member 56 can be advantageously customized depending upon the construction (e.g., length, width, thickness, etc.) of the inflatable guide member so that the angle A is different from the angle that is naturally formed by the bevel associated with the opening 34 of the laryngeal mask 16.

In another aspect, the airway device 10 includes an endotracheal tube 18 (FIG. 1) that is slidably disposed within the first passageway 22 of the tubular guide 14. By "slidably disposed", it is meant that the endotracheal tube 18 is not fixed within the first passageway 22 so that it is incapable of telescoping through the tubular guide 14. Rather, the term "slidably disposed" can mean that the endotracheal tube 18 is translatable along a longitudinal axis of the first passageway 22 (e.g., using tactile force). In some instances, all or substantially all of the entire length of the endotracheal tube 18 can extend through the first passageway 22.

The endotracheal tube 18 can be sized and dimensioned to ventilate a patient requiring anesthesia and/or respiratory assistance. In some instances, the endotracheal tube 18 can comprise a plastic tube that can be passed through the supra-glottic airway support 12, past the vocal cords, and lodged in the trachea proximal (or above) the lungs. The endotracheal tube 18 can include a distal end 64, a proximal end 66, and a second passageway (not shown) that extends between the distal and proximal ends. Since the tubular guide 14 is sized and dimensioned to receive the endotracheal tube 18, a diameter associated with the first passageway 22 can be greater than a diameter associated with the second passageway. In some instances, when the endotracheal tube 18 disposed in the first passageway 22, the second passageway and the first passageway are concentric or coaxial with one another. In other instances, the first passageway 22 is not concentric with the second passageway when the endotracheal tube 18 is disposed within the tubular guide 14. For example, where the tubular guide 14 has a non-circular cross-sectional profile (e.g., an oblong cross-sectional profile), the endotracheal tube 18 (and thus the second passageway) can be axially offset from, or non-concentric with, the first passageway 22.

The endotracheal tube 18 can include a cuff 68 or balloon portion surrounding the circumference of the endotracheal tube near the distal end 64 that rests in the patient's trachea. The cuff 68 can be inflated to seal against the wall of the trachea after the endotracheal tube 18 has been properly inserted into a subject. Once sealed, positive pressure ventilation may be used to provide respiratory assistance and, if desired, anesthesia or other gas, gas mix, etc., to the patient though the endotracheal tube 18 via a ventilator (not shown). The cuff 68 provides a seal that tends to block liquids and solids from passing along the outside of the endotracheal tube 18 between the tube and trachea wall and entering the patient's lungs. The endotracheal tube 18 can further include an inflation tube 70 (FIG. 6) and an air valve 72 for inflating and deflating the cuff 68.

In another aspect, the airway device 10 includes a sealing mechanism configured to occlude the flow of a gas, gas mix, etc., through the first passageway 22. The sealing mechanism imparts the airway device 10 with the ability to change from the supra-glottic airway support 12 to an endotracheal tube 18 (and back again) by providing a single, common airway (i.e., the second passageway) that is not disrupted or stopped when the ventilation needs of the patient change. In some instances, the sealing mechanism can include one or more sealing members 98 (FIG. 7B) configured to directly contact, and encircle, a portion of the outer surface of the endotracheal tube 18 (as disclosed in the '343 application). In other instances, the distal cuff 68 of the endotracheal tube 18 can serve as the sealing mechanism. For example, when the distal cuff 68 of the endotracheal tube 18 is disposed within the distal end portion 20 of the tubular guide 14, the distal cuff can be inflated to occlude the first passageway 22 and thereby force a gas, gas mix, etc., to flow through the second passageway of the endotracheal tube.

Figure 7A:
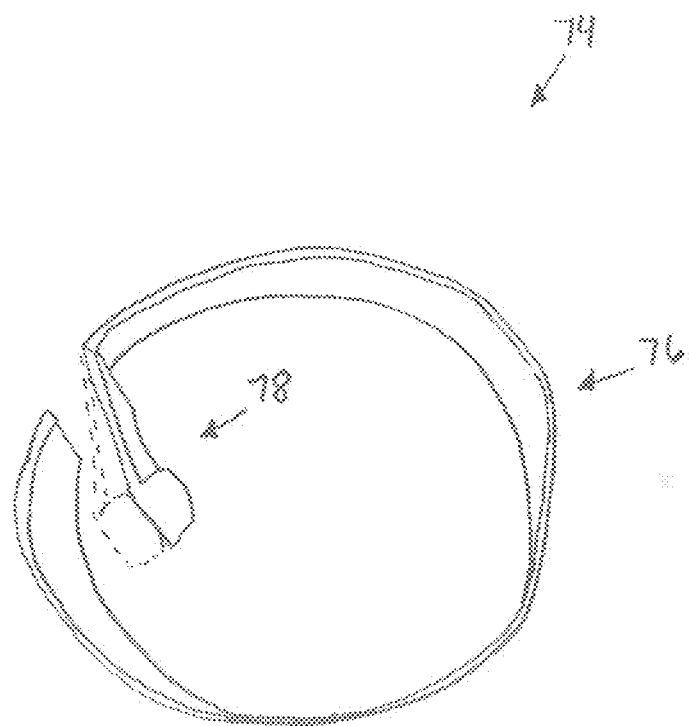
FIG. 7A is a perspective view showing a ring-shaped clip adapted for use with the reversible airway device in FIG. 1.
Figure 7B:
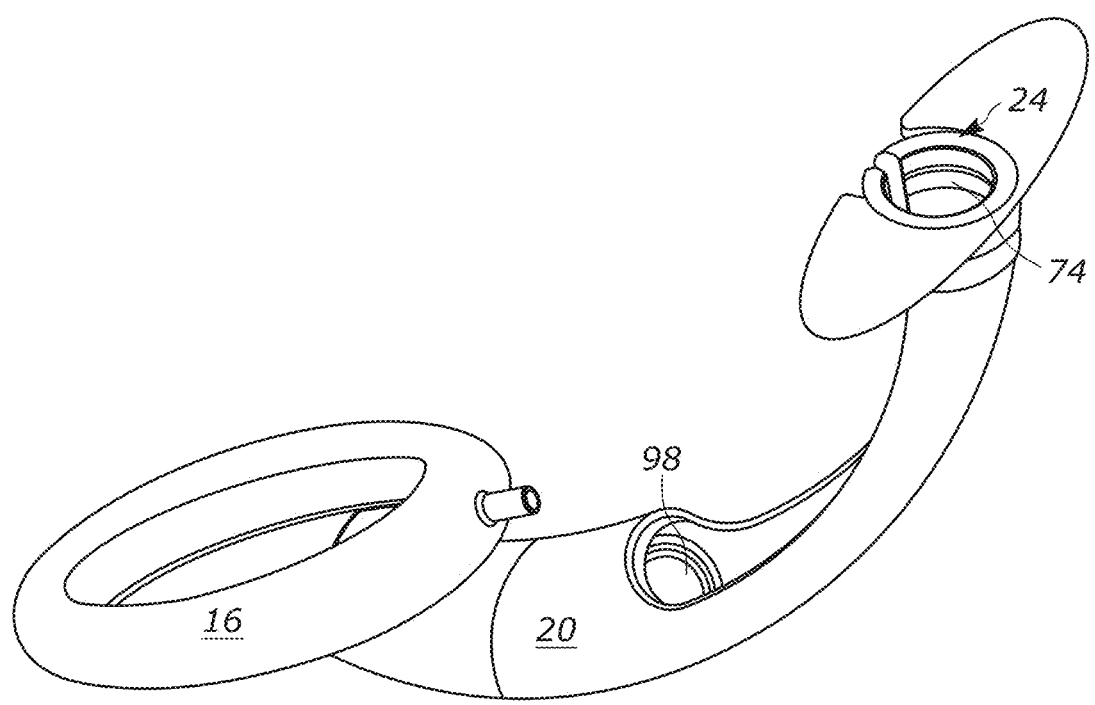
FIG. 7B is a perspective view showing the ring-shaped clip in FIG. 7A mated with a proximal end portion of the reversible airway device of FIG. 1.

In another aspect, the airway device 10 can additionally or optionally include a clip 74 configured to maintain the endotracheal tube 18 in the center of the first passageway 22. The ability of the clip 74 to maintain the endotracheal tube 18 in the center of the first passageway 22 is advantageous because it ensures proper positioning of the endotracheal tube within the tubular guide 14 such that a physician can quickly and effectively guide the endotracheal tube during use of the airway device 10 without unwanted rubbing with, or obstruction by, the inner surface of the tubular guide. The clip 74 can be sized and dimensioned to fit within a proximal end portion 24 of the tubular guide 14 (FIG. 7B). The clip 74 (FIG. 7A) can include a body 76 having an incomplete or discontinuous ring shape, and a flexible finger 78 that is connected thereto and extends towards the center of the body. The flexible finger 78 is flexible so that it can be automatically biased from a first position (dashed lines) to a second position. The endotracheal tube 18 can be easily inserted into the first passageway 22 of the tubular guide 14 by retaining the finger 78 in the first position. After inserting the endotracheal tube 18 into the first passageway 22, the finger 78 can be released so that it automatically obtains the second position and radially displaces the endotracheal tube into the center of the first passageway.

Methods

Another aspect of the present disclosure includes a method 80 (FIG. 8) for easing transition of a sedated, intubated patient to wakefulness. When transitioning an intubated and sedated patient to wakefulness, it is important to maintain both the patient's airway and connection to a ventilation source. Current methods for doing so involve using different devices that risk the danger of disconnection and/or loss of the airway. As described below, the method 80 of the present disclosure advantageously provides a technique for providing uninterrupted, continuous ventilation while maintaining the airway of a subject to improve the transition to wakefulness.

Figure 8:
FIG. 8 is a process flow diagram illustrating a method for easing transition of a sedated, intubated patient to wakefulness according to another aspect of the present disclosure.
Figure 9:
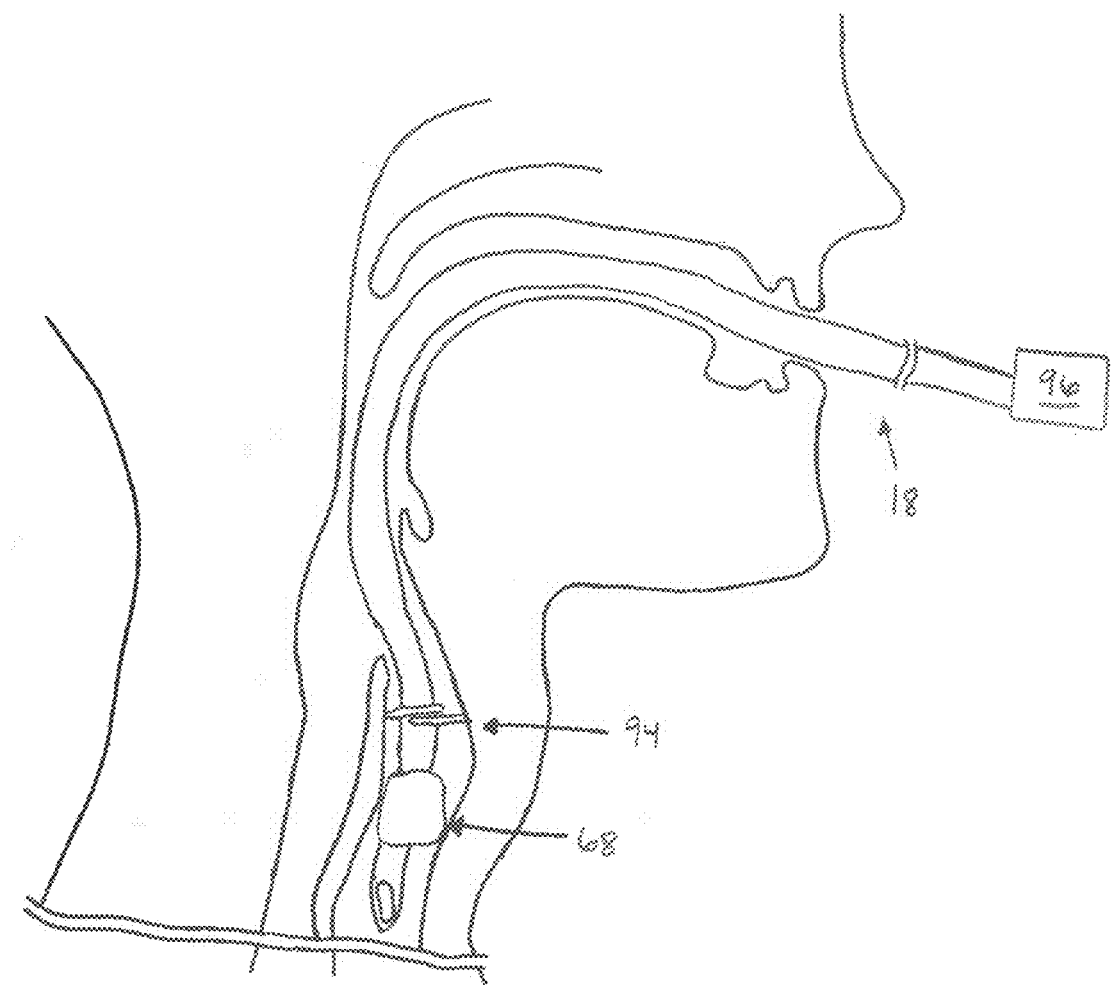
FIG. 9 is a cross-sectional view of a patient intubated with an endotracheal tube.
Figure 10:
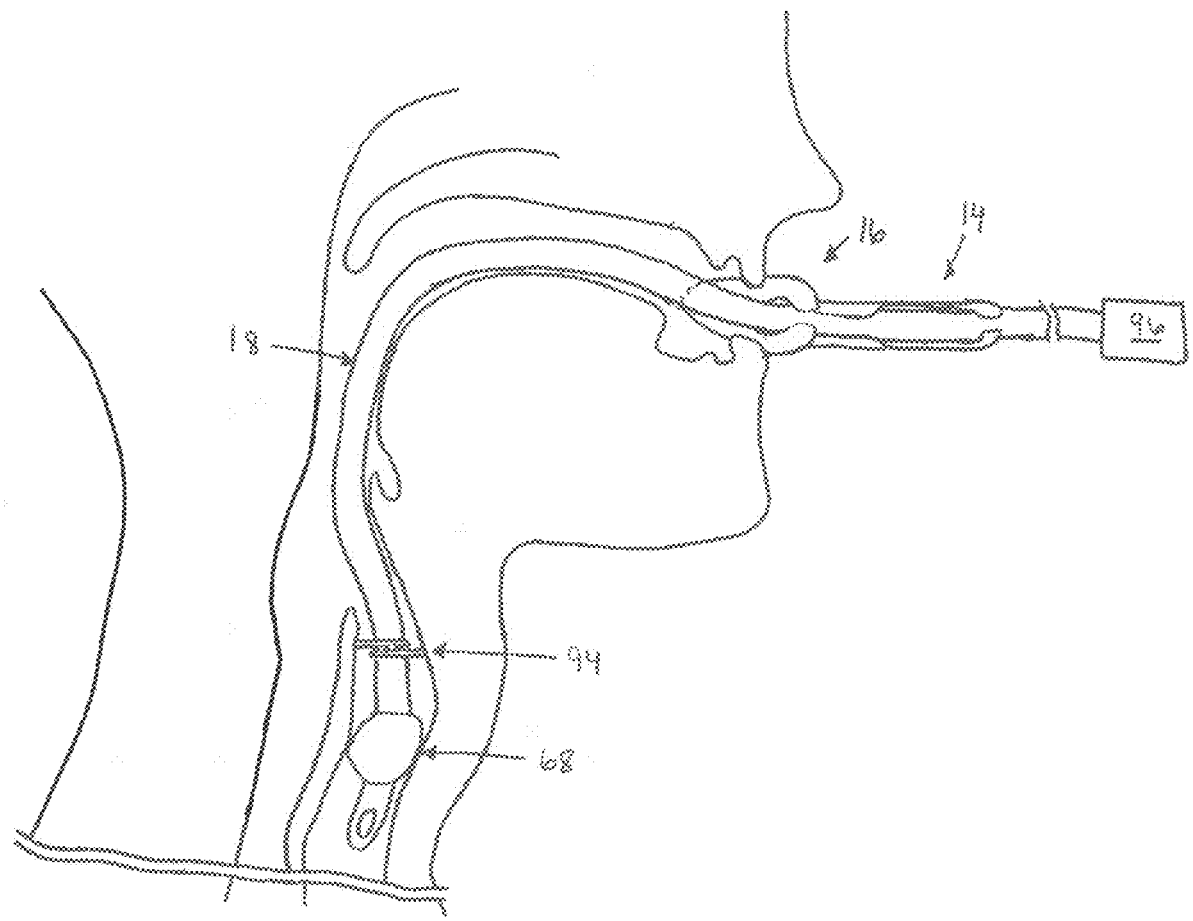
FIG. 10 is a schematic illustration showing a tubular guide of the present disclosure being inserted over the endotracheal tube in FIG. 9.
Figure 11:
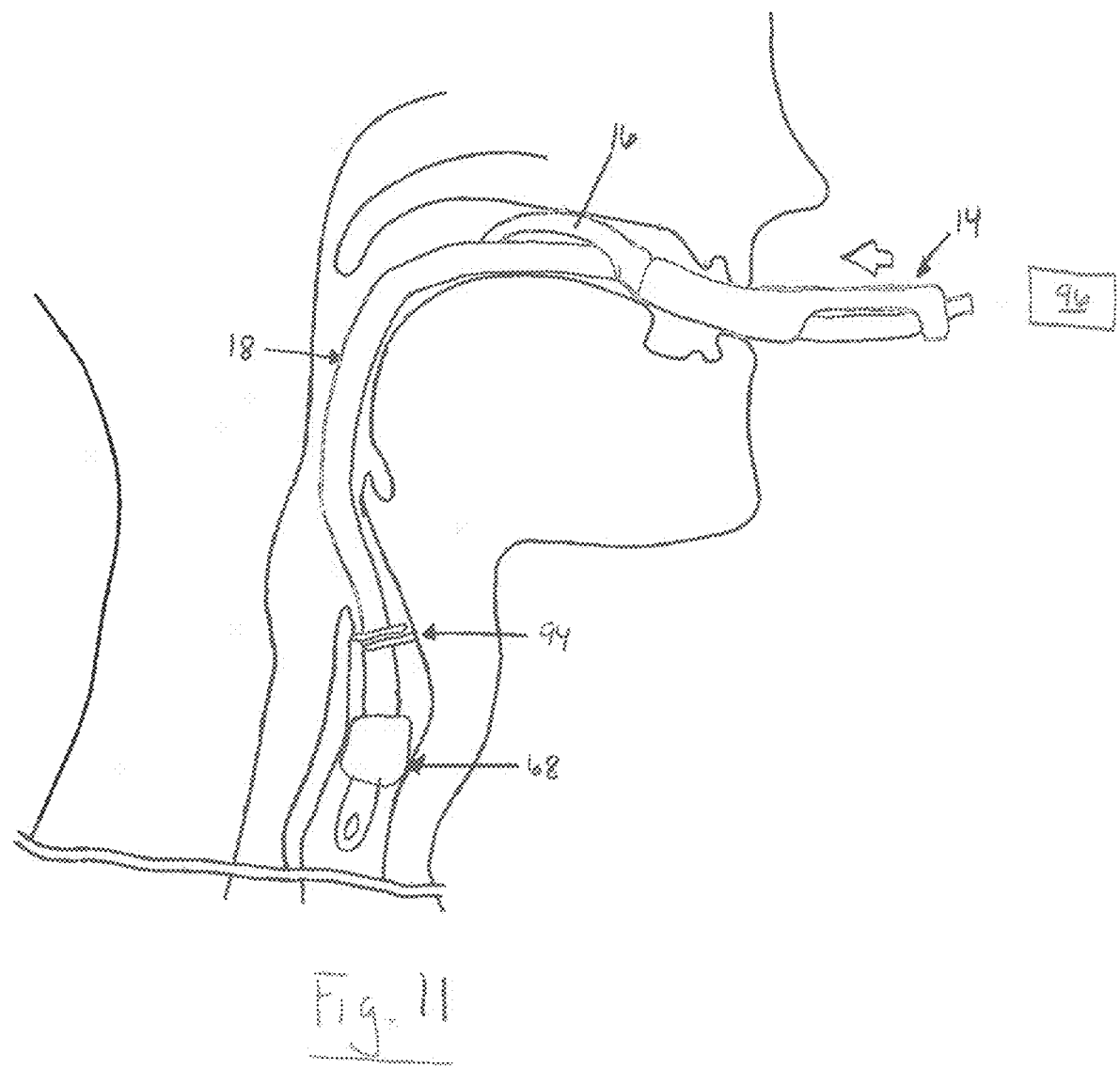
FIG. 11 is a schematic illustration showing an alternative configuration of the tubular guide of the present disclosure being inserted over the endotracheal tube in FIG. 9.
Figure 12:
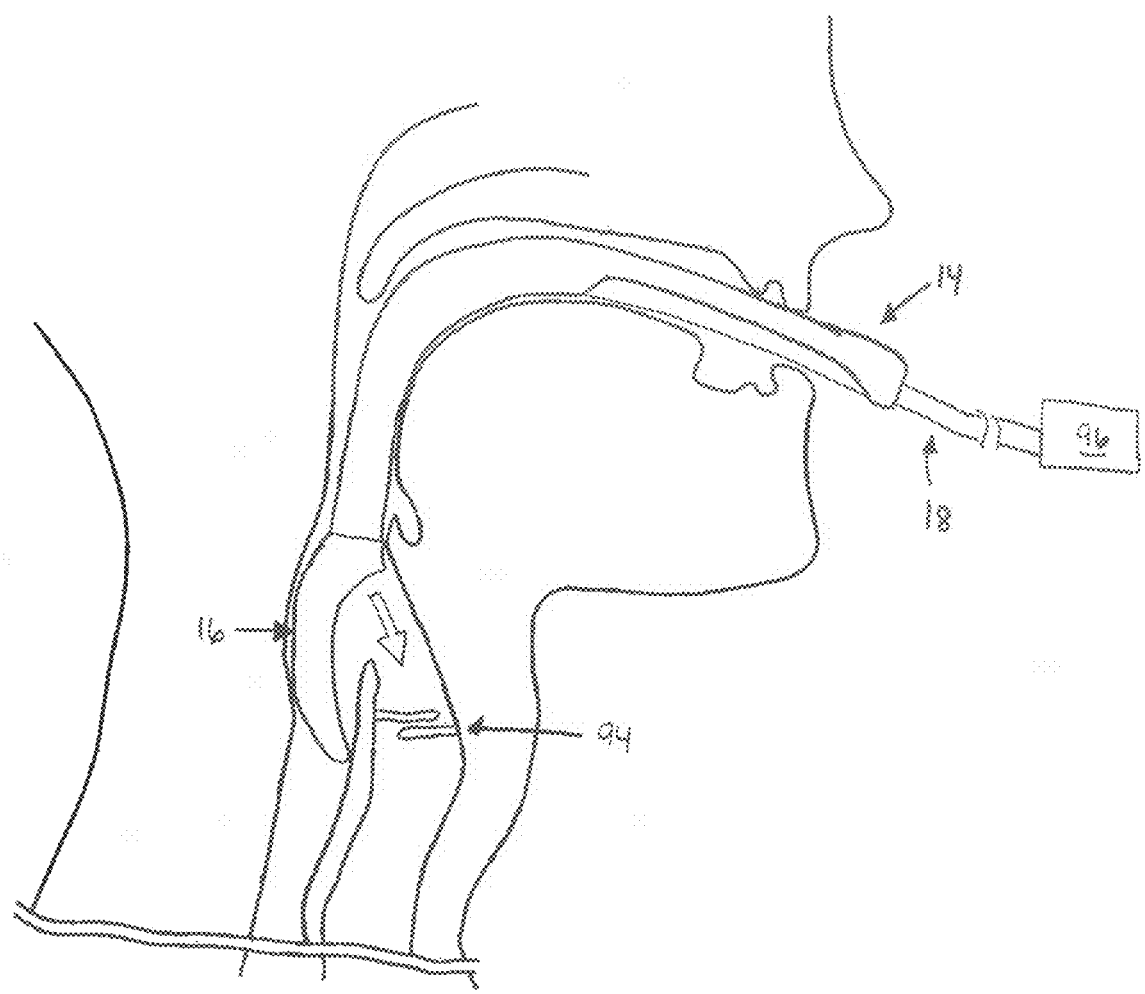
FIG. 12 is a schematic illustration showing reversible airway device of FIG. 1 implanted in the airway of the patient.

As shown in FIG. 8, the method 80 can generally include the steps of providing a reversible airway device 10 (Step 82), placing a tubular guide 14 of the airway device over an endotracheal tube 18 (Step 84), advancing the tubular guide over the endotracheal tube (Step 86), inflating a laryngeal mask 16 of the airway device (Step 88), withdrawing the endotracheal tube (Step 90), and optionally inflating a distal cuff 68 of the endotracheal tube (Step 92). Referring to FIGS. 9-11, a patient is shown schematically with the mouth open in cross-section and leading to the back of the throat (sometimes the mouth and/or throat are referred to as the oral cavity of the patient), and from there to the trachea via the laryngeal inlet, which provides an airway that leads to the lungs.

At Step 82, the method 80 can include providing a reversible airway device 10. The reversible airway device 10 can be constructed in an identical or similar manner as shown in FIG. 1 and described above. For the purpose of illustration only, the method 80 will be described below using the airway device 10 of FIG. 1. It will be appreciated that the airway device 10 can be sized and dimensioned to accommodate a variety of patient sizes, such as pediatric patients.

FIG. 9 shows a sedated patient intubated with an endotracheal tube 18. The distal cuff 68 of the endotracheal tube 18 is positioned below the vocal cords 94 and inflated to permit the flow of gas, air, etc. through the second passageway of the endotracheal tube. The proximal end 66 of the endotracheal tube 18 is operably connected to a ventilation source 96, which continuously ventilates the sedated patient. When sedation is no longer desired, the transition to wakefulness can begin by placing the tubular guide 14 of the airway device 10 over the endotracheal tube 18 (Step 84). In some instances, Step 84 can be done under direct fiberoptic view. As shown in FIG. 10, this can include separating the distal end portion 20 of the tubular guide 14 and the laryngeal mask 16 at the first and second longitudinal seams 28 and 36 (respectively). After separating the first and second longitudinal seams 28 and 36, the endotracheal tube 18 and the tubular guide 14 can be mated so that the endotracheal tube resides in the first passageway 22. Where the airway device 10 includes a sleeve 30, it will be appreciated that the sleeve can be removed prior to separating the first and second longitudinal seams 28 and 36.

It will also be appreciated that Step 84 can include placing the tubular guide 14 over the endotracheal tube 18 as shown in FIG. 11. For example, the proximal end 66 of the endotracheal tube 18 can be briefly disconnected from the ventilation source 96, whereafter the proximal end is inserted into the opening 34 of the laryngeal mask 16. The tubular guide 14 can then be progressively fed over the endotracheal tube 18 into the patient's airway.

At Step 86, the laryngeal mask 16 and the tubular guide 14 can be advanced into the airway of the patient. For example, the laryngeal mask 16 can be positioned in the patient so that a lower portion of the laryngeal mask 16 substantially blocks the esophagus to minimize the risk of regurgitation of stomach contents and the passage of air into the stomach. An upper portion 38 of the laryngeal mask 16 also guides the distal end portion 29 of the tubular guide 14 into alignment using the laryngeal inlet of the patient as a guide to insert along the patient's airway.

Once inserted, the inflatable portion 40 of the laryngeal mask 16 can be inflated through the inflation tube 52 so that the upper portion 38 of the laryngeal mask substantially fills the patient's laryngopharynx at the level of the laryngeal inlet (Step 88). Consequently, the upper portion 38 of the laryngeal mask 16 surrounds the laryngeal inlet so that the opening 34 of the laryngeal mask is substantially sealed in fluid communication with the laryngeal inlet, e.g., pressing against walls of the oral cavity portions of the patient.

At Step 90, intubation can be terminated by deflating the distal cuff 68 of the endotracheal tube 18 and at least partially withdrawing the endotracheal tube into the tubular guide 14. Since an airtight seal is still maintained between the laryngeal mask 16 and the laryngeal outlet, ventilation of the patient can continue uninterrupted through the second passageway upon discontinuing ventilation with the endotracheal tube 18. Ventilation can continue by virtue of the sealing mechanism described above. Where the sealing mechanism comprises a sealing member that encircles the outer surface of the endotracheal tube 18, for example, fluid movement through the first passageway 22 is prevented and ventilation can continue through the second passageway. Alternatively, the distal cuff 68 of the endotracheal tube 18 can serve as the sealing mechanism by inflating the distal cuff within the distal end portion 29 of the tubular guide 14 so that fluid movement through the first passageway 22 is prevented and ventilation can continue through the second passageway (Step 92). Now that the patient is no longer intubated, ventilation can proceed through the tubular guide 14 (and the laryngeal mask 16) to ease the patient's transition to wakefulness.

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The invention claimed is:

1. A reversible airway device comprising:
   a tubular guide having a distal end portion, a proximal end portion, and a first passageway extending between the distal and proximal end portions, the tubular guide further including a first longitudinal seam;
   a longitudinal slot partially extending between the distal end portion and the proximal end portion of the tubular guide;
   a laryngeal mask attached to the distal end portion of the tubular guide, the laryngeal mask including an opening in fluid communication with the first passageway, the laryngeal mask further including a second longitudinal seam; and
   an endotracheal tube slidably disposed within the first passageway;
   wherein the first and second longitudinal seams are adapted to permit ingress and egress of the tubular guide from the airway without detaching the endotracheal tube from a ventilation source; and
   wherein the first longitudinal seam has two first edges that abut one another to form the first longitudinal seam and/or the second longitudinal seam has two second edges that abut one another to form the second longitudinal seam.

2. The airway device of claim 1, wherein a sealing mechanism is disposed within the first passageway and configured to occlude the flow of a gas through the first passageway.

3. The airway device of claim 1, wherein the first and second longitudinal seams form a single, continuous seam.

4. The airway device of claim 1, wherein the first longitudinal seam extends across the distal end portion of the tubular guide.

5. The airway device of claim 1, further comprising a removable sleeve slidably disposed about the distal end portion of the tubular guide, the sleeve being configured to prevent unintended separation of the first longitudinal seam and/or the second longitudinal seam.

6. The airway device of claim 1, wherein the endotracheal tube has a second passageway that is concentric with the first passageway.

7. The airway device of claim 1, wherein the endotracheal tube has a second passageway that is not concentric with the first passageway.

8. The airway device of claim 1, wherein the first longitudinal seam is formed by overlapping a first free end portion adjacent the first edge with a second free end portion adjacent the second edge.

9. The airway device of claim 1, wherein the abutting first edges are separated to permit ingress and egress of the tubular guide from the airway and/or the abutting second edges are separated to permit ingress and egress of the tubular guide from the airway.

10. The airway device of claim 1, wherein an inflatable cuff of the laryngeal mask includes opposing first and second free end portions that, when joined together, form the second longitudinal seam.

11. The airway device of claim 10, wherein the first and second free end portions are crimped together to form the second longitudinal seam.

12. The airway device of claim 10, wherein the first and second free end portions include a connecting mechanism, the connecting mechanism comprising a connecting member associated with the first free end portion and a port member associated with the second free end portion configured to receive the connecting member.

* * * * *